United States Patent
Brown et al.

(10) Patent No.: US 7,268,871 B2
(45) Date of Patent: Sep. 11, 2007

(54) MEASURING HEAD FOR PLANAR MEASUREMENT OF A SAMPLE

(75) Inventors: Lawrence B. Brown, Cochranville, PA (US); Rudiger Kubitzek, Geilenkirchen (DE); Alan Ingleson, Newbury (GB); Joseph Reed, Carversville, PA (US)

(73) Assignee: Datacolor Holding AG, Lucerne (CH)

( * ) Notice: Subject to any disclaimer, the term of this patent is extended or adjusted under 35 U.S.C. 154(b) by 232 days.

(21) Appl. No.: 10/916,762

(22) Filed: Aug. 12, 2004

(65) Prior Publication Data

US 2006/0033911 A1    Feb. 16, 2006

(51) Int. Cl.
*G01J 3/28*    (2006.01)
*G01J 3/44*    (2006.01)
(52) U.S. Cl. .................... 356/326; 356/301
(58) Field of Classification Search ............... 356/73.1, 356/300–334; 353/326; 600/166, 178
See application file for complete search history.

(56) References Cited

U.S. PATENT DOCUMENTS

| | | | |
|---|---|---|---|
| 4,646,721 A * | 3/1987 | Arakawa | 600/130 |
| 4,881,811 A * | 11/1989 | O'Brien | 356/323 |
| 4,963,728 A * | 10/1990 | Hof et al. | 250/227.11 |
| 5,815,254 A | 9/1998 | Greene | |
| 5,892,630 A * | 4/1999 | Broome | 359/834 |
| 6,008,905 A * | 12/1999 | Breton et al. | 356/402 |
| 6,069,689 A * | 5/2000 | Zeng et al. | 356/73 |
| 6,119,031 A * | 9/2000 | Crowley | 600/407 |
| 6,527,708 B1 * | 3/2003 | Nakamura et al. | 600/160 |
| 6,570,657 B1 * | 5/2003 | Hoppe et al. | 356/445 |
| 6,720,526 B2 * | 4/2004 | Horsting et al. | 219/121.71 |

* cited by examiner

*Primary Examiner*—Gregory J. Toatley, Jr.
*Assistant Examiner*—Jarreas Underwood
(74) *Attorney, Agent, or Firm*—Kin-Wah Tong, Esq.; Patterson & Sheridan LLP

(57) ABSTRACT

A measuring head of the present invention conveys light from an external source through at least one optical fiber to at least one respective plane mirror inside the measuring head, where the light reflects through and is collimated by at least one collimating lens so as to be incident on a sample, in one embodiment, at an angle of substantially 45 degrees. The resulting optical path is folded once and thereby allows enough virtual space to redirect the light without excessive bending of the fibers. Light diffused from the sample is, in one embodiment, perpendicularly collected by a focusing lens, focused on the end of another optical fiber and directed outside of the measuring head to be used, for example, by a measuring instrument for the spectral analysis of the collected light.

20 Claims, 4 Drawing Sheets

MEASURING HEAD FOR PLANAR MEASUREMENT OF A SAMPLE

BACKGROUND OF THE INVENTION

1. Field of the Invention

The present invention relates generally to a measuring head and, more specifically, to a measuring head implementing light guides for the planar measurement of a sample.

2. Description of the Related Art

Conventional measuring heads typically include an optical projection means to illuminate a measuring surface and optical measuring means for measuring the light reflected. An example of such a measuring head is described in U.S. Pat. No. 4,078,858, which comprises an incandescent lamp, which in order to produce a measuring spot is associated with a collimator lens and a deviation mirror, together with a further collecting lens. The light reflected by the measuring spot at an angle of 45 degrees arrives in the optical measuring means, which comprises a spherical annual mirror and a flat spherical mirror.

One application of such conventional measuring heads is described in an apparatus to determine the optical density of photographs described in U.S. Pat. No. 3,244,062, which comprises a measuring head with an optical projection means, which images the light of an incandescent lamp on the photographic material and an optical measuring means which captures the light re-scattered essentially perpendicularly from the photographic surface by means of a deviating mirror transversely to the optical axis of the optical projection means and exposes the inlet aperture of a photoelectron multiplier with the aid of a lens. The optical projection means makes it possible to expose the measuring spot, at an angle of incidence of essentially 45 degrees on all sides, to the light originating in the incandescent light in the measuring head. The optical projection means correlated with the incandescent lamp contains a spherical annular mirror, which surrounds the incandescent lamp, with the filament of said lamp extending along the optical axis of the spherical annual mirror. The light of the lamp passing from the spherical annular mirror parallel to the optical axis of the optical projection means is focused by means of a simple annular mirror onto the measuring surface. The quality of the optical projection means and the optical measuring device of the known apparatus is adequate for simple density measurements in the determination of optical reflection properties, however is not adequate for detailed spectral analysis of the light reflected. Such conventional measuring heads convey large amounts of stray light and crosstalk in a reflected signal and typically require high-power light sources because of the loss of light in the optical cavity due to scattering.

In addition, conventional measuring heads which do not contain light sources within their housings require very specific alignment with respect to an outside light source for the collection of light from the light source to ultimately illuminate a sample. Such specific alignment procedures may prove to be very difficult and time consuming.

SUMMARY OF THE INVENTION

The present invention addresses various deficiencies in the prior art by providing an improved measuring head for illuminating a measuring surface and passing the measuring light reflected from a measuring spot to a measuring device with adequate precision and intensity, in order to, for example, carry out a spectral analysis of the light reflected.

The measuring head of the present invention provides flexibility in the positioning of the measuring head with respect to a light source such that the position of the measuring head may be varied along a measuring surface without the reduction of the intensity with which the measuring surface is illuminated.

In one embodiment of the present invention, a measuring head includes at least one input light guide for conveying light from an external light source to the measuring head for the illumination of a sample, at least one collimating optic for collimating the conveyed light from the external light source, at least one plane mirror for reflecting the conveyed light from said external light source such that an optical path of the conveyed light is folded at least once within the measuring head, at least one focusing optic for focusing the diffused light from the illuminated sample, and at least one output light guide for collecting the focused light and conveying the collected light outside of the measuring head.

The folded optical path of the measuring head allows for a great reduction in the size of the measuring head 100 of the present invention compared to conventional measuring heads currently available. That is, the folded optical path allows enough virtual space to redirect the light without excessive bending of the fibers in a relatively small sized measuring head. Furthermore the input and output fibers of the present invention reduce the amount of stray (re-directed) light inside of the housing of a measuring head in accordance with the present invention. Such a reduction in stray light allows for more accurate measurement and analysis of the collected light carried outside of the measuring head by the at least one output optical fiber. The input optical fibers also provide flexibility in the positioning of a measuring head with respect to a light source used for illuminating a sample.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures.

DETAILED DESCRIPTION

The present invention advantageously provides a measuring head for conveying light from a source through at least one light guide (e.g., optical fiber) to plane mirrors inside the measuring head, where the light reflects through at least one collimating lens so as to be incident on a sample, in one embodiment, at an angle of substantially 45 degrees. Light diffused from the sample is perpendicularly collected by another lens, focused on the end of another light guide (e.g., optical fiber) and directed outside of the measuring head. Although various embodiments of the present invention are described herein with respect to a measuring head comprising a specific number of respective collection fibers, flat mirrors and collimating lenses, the specific embodiments of the present invention should not be treated as limiting the scope of the invention. It will be appreciated by those skilled in the art informed by the teachings of the present invention that the concepts of the present invention may be advantageously applied to providing a measuring head having substantially any number or combinations of collection fibers, flat mirrors and collimating lenses.

Figure 1:
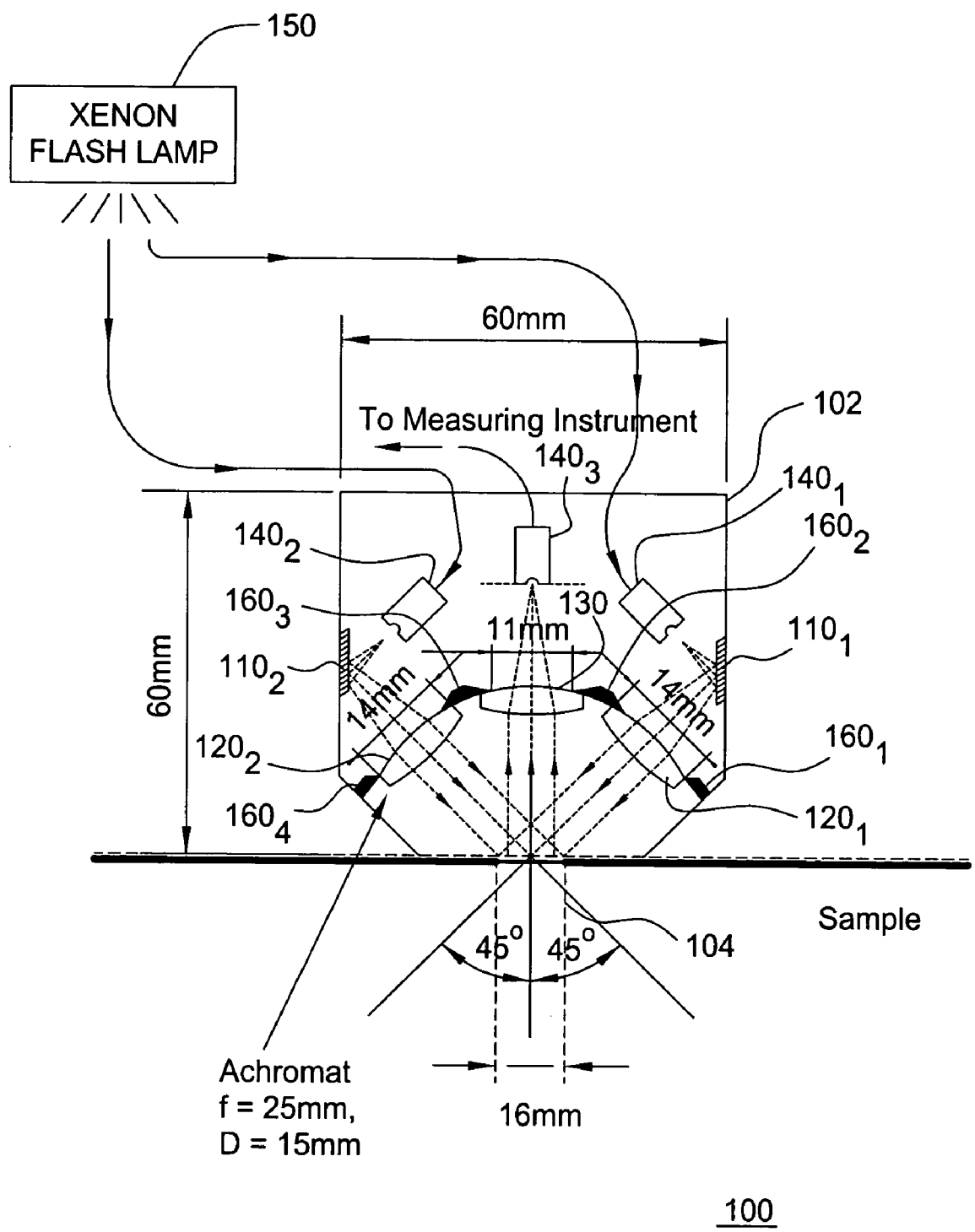
FIG. 1 depicts a high level block diagram of an embodiment of a measuring head in accordance with the present invention.

FIG. 1 depicts a high level block diagram of an embodiment of a measuring head in accordance with the present invention. The measuring head 100 of FIG. 1 illustratively comprises a housing 102 having a sampling aperture 104 on a front face. The measuring head 100 further comprises two flat mirrors $110_1$-$110_2$ illustratively located 180 degrees apart on opposite side walls, two collimating optics $120_1$-$120_2$ (illustratively a respective collimating lens for each flat mirror), a focusing optic 130 (illustratively a focusing lens) and three light guides (illustratively three optical fibers) $140_1$-$140_3$. FIG. 1 further depicts an incandescent light source (illustratively a Xenon flash lamp) 150. The light source 150 may be included as a component to be used with the measuring head 100 or may be provided by a user.

In the measuring head 100 of FIG. 1, light from the Xenon lamp 150 is collected by two of the optical fibers (input optical fibers), illustratively optical fibers $140_1$ and $140_2$. The light from the Xenon lamp 150 collected by each of the input optical fibers $140_1$, $140_2$ is directed to a respective flat mirror $110_1$, $110_2$ of the measuring head 100. The light from the respective input fibers $140_1$, $140_2$ reflects off of the respective flat mirror $110_1$, $110_2$ to a respective collimating lens $120_1$, $120_2$. The light collimated by the respective collimating lenses $120_1$, $120_2$ illuminates a sample via the sampling aperture 104 of the housing 102 of the measuring head 100. Diffused light generated by the illumination of the sample via the aperture 104 is collected perpendicularly and focused by the focusing lens 130. The focused, diffused light is collected by the third optical fiber $140_3$ (output optical fiber), which carries the collected light outside of the measuring head. The light in the output optical fiber $140_3$ is carried outside of the measuring head by the fiber to be used, for example, by a measuring instrument for the spectral analysis of the collected light. Although in the measuring head 100 of FIG. 1, the output optical fiber $140_3$ is depicted as being at least partially located within the measuring head 100 and as such included as a component of the measuring head, in alternate embodiments of the present invention, a focusing lens for collecting and focusing the diffused light from the illuminated sample may be chosen such that the collected, diffused light is focused at a position just outside of the measuring head and as such may be collected by a collection means, such as an optical light guide, at a position outside of the measuring head. Therefore, an output light guide need not be positioned within the measuring head and would not be a required component of a measuring head of the present invention itself but may be provided by a user.

In the measuring head 100 of FIG. 1, the input optical fibers $140_1$ and $140_2$, the flat mirrors $110_1$ and $110_2$ and the collimating lenses $120_1$ and $120_2$ are positioned and located such that a sample is illuminated by a collimated beam of light from the Xenon lamp 150 at an angle of substantially 45°+/−2°. Furthermore, the focusing lens is positioned and located such that the diffused light from an illuminated sample is focused by the focusing lens 130 and collected by the output optical fiber $140_3$ at an angle of substantially 0°+/−0.5°.

More specifically, the input optical fibers $140_1$ and $140_2$ are positioned in the housing 102 of the measuring head 100 such that the light from the Xenon lamp 150 carried by the input fibers $140_1$, $140_2$ reflects off of the respective flat mirrors $110_1$, $110_2$ at an angle of substantially 45°+/−2°. The collimating lenses $120_1$, $120_2$ are respectively positioned in the housing 102 of the measuring head 100 such that the reflected Xenon light from the respective flat mirrors $110_1$, $110_2$ is collimated and illuminates a sample via the sampling aperture 104 of the housing 102 of the measuring head 100 at an angle of substantially 45°+/−2°. The focusing lens 130 is positioned in the housing 102 of the measuring head 100 such that diffused light from an illuminated sample is collected at an angle of substantially 0°+/−0.5°. Subsequently, the output optical fiber $140_3$ is positioned at the focal point of the focusing lens 130 to perpendicularly collect the focused, diffused light from the illuminated sample.

As depicted in the measuring head 100 of FIG. 1, The resulting optical path is folded once (i.e., the light is incident to the flat mirror at substantially a 45 degree angle and reflects off of the flat mirror at substantially a 45 degree angle). Such a configuration allows for a great reduction in the size of the measuring head 100 of the present invention compared to conventional measuring heads currently available. That is, the folded optical path allows enough virtual space to redirect the light without excessive bending of the fibers in a relatively small sized measuring head.

The physical and optical properties of the various components of the measuring head 100 are defined by, at least, the desired dimensions of the measuring head 100 and the position of the components within the housing 102 of the measuring head 100. For example, in the measuring head 100 of FIG. 1, the length and width of the housing 102 of the measuring head illustratively both measure sixty (60) millimeters. In addition, the sampling aperture 104 of the housing 102 of the measuring head 100 of FIG. 1 illustratively measures sixteen (16) millimeters in width. As such, in FIG. 1, the numerical aperture and position of the input optical fibers $140_1$, $140_2$ and the size, position, and curvature of the collimating lenses $120_1$, $120_2$ are selected such that Xenon light from the optical fibers $140_1$, $140_2$, reflected by the flat mirrors $110_1$, $110_2$ and collimated by the collimating lens lenses $120_1$, $120_2$ illuminate the entire sampling aperture 104, and thus the portion of the sample within the sampling aperture, of the housing 102 of the measuring head 100 of FIG. 1. For example, in the measuring head 100 of FIG. 1, the first and second input optical fibers $140_1$, $140_2$ each illustratively comprise a single four hundred (400) micron fiber having a numerical aperture of 0.39 (i.e., the sine of the half-angle of the exit). The first and second collimating lenses each have a focal length of 25 mm and a diameter of 15 mm. The aperture 104 of the measuring head 100 comprises an opening in the housing 102 of 16 mm and, as such, the perpendicularly diffused light from an illuminated sample also comprises a collimated beam measuring substantially 11 mm in width. In the measuring head 100 of FIG. 1, a substantially similar lens as the lenses used for the collimating lenses $120_1$, $120_2$ of the measuring head 100 is used as the focusing lens 130. More specifically, the focusing lens 130 has a focal length of 25 mm and a diameter of 15 mm. The output optical fiber $140_3$ is a single four hundred (400) micron fiber having a numerical aperture of 0.39 and is positioned within the housing 102 of the measuring head 100 at the position of the focus of the focusing lens 130.

As described above, in a measuring head in accordance with an embodiment of the present invention, the at least one input optical fiber(s) directs the light from the light source to a sample via at least one flat mirror and at least one collimating lens. The at least one output optical fiber collects the focused diffused light from the sample and directs the light outside of the measuring head. The use of the optical fibers to direct the light in and out of the measuring head reduces the amount of stray (re-directed) light inside the housing of the measuring head. Such a reduction in stray light allows for more accurate measurement and analysis of the collected light carried outside of the measuring head by the at least one output optical fiber.

Referring back to FIG. 1, to further reduce the effects of stray light in the optical path, the measuring head 100 may optionally further comprise a plurality of light baffles. For example and as depicted in FIG. 1, light baffles $160_1$-$160_4$ may be located at the edges of each of the collimating $120_1$, $120_2$ and the focusing 130 lenses to reduce the amount of redirected light in the measuring head 100 and to reduce the negative effects of optical aberrations that may occur at the edges of the lenses. To further reduce stray light, the interior of the housing of the measuring head 100 may be coated with a black matte material.

Figure 2:
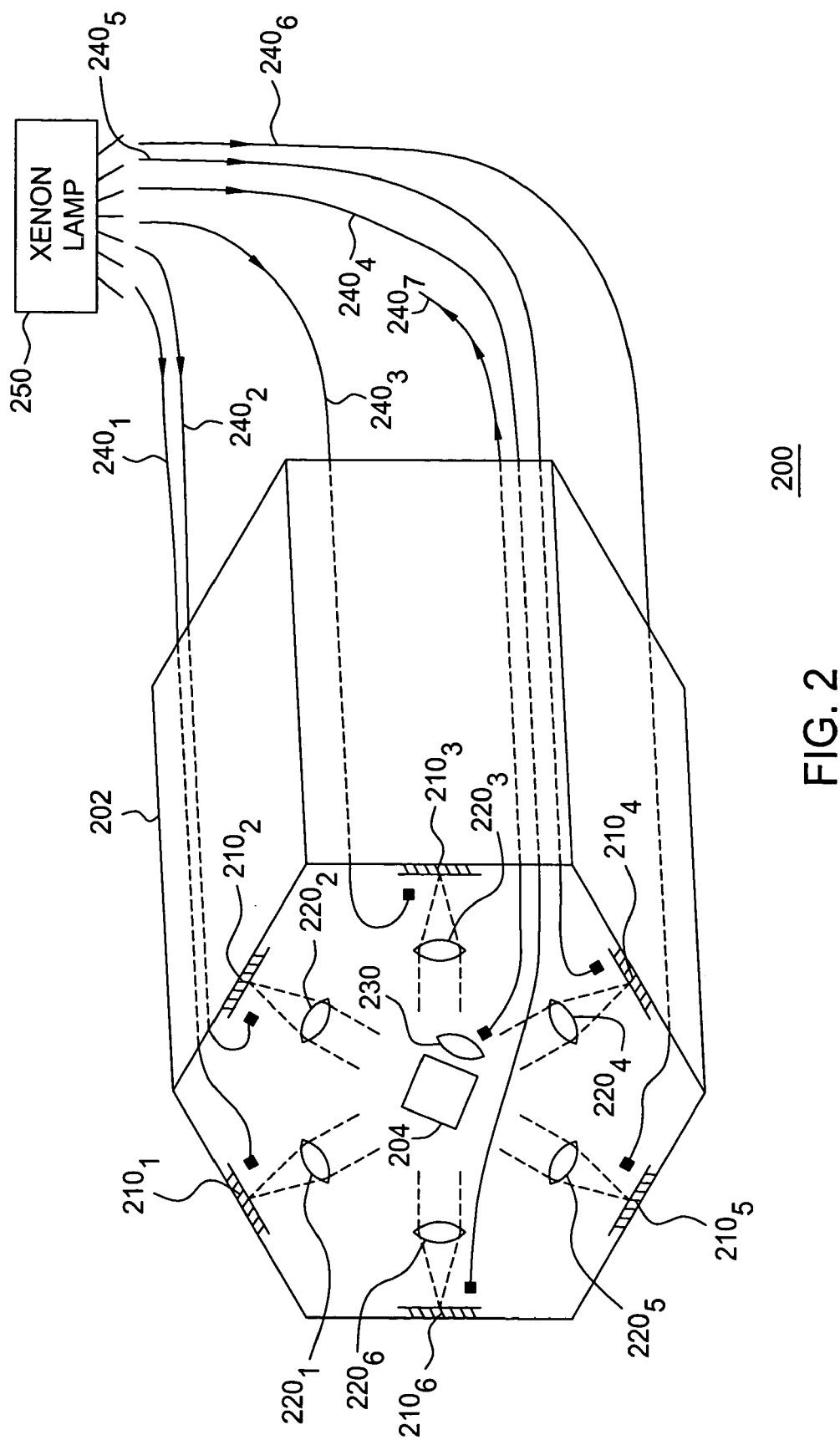
FIG. 2 depicts a high level block diagram of an alternate embodiment of a measuring head in accordance with the present invention.

Although the measuring head 100 of FIG. 1 is depicted as comprising two flat mirrors $110_1$ and $110_2$, two collimating lenses $120_1$ and $120_2$, and two input optical fibers $140_1$ and $140_2$ for directing the light from the Xenon lamp 150 to illuminate the sample, in alternate embodiments of the present invention, a measuring head of the present invention may comprise substantially any numbers or combinations of flat mirrors, collimating lenses and optical fibers for collecting light from the light source. Additionally, a measuring head of the present invention may comprise substantially any numbers of output optical fibers for conveying the perpendicularly collected light from the illuminated sample outside of the measuring head. For example, FIG. 2 depicts a high level block diagram of an alternate embodiment of a measuring head in accordance with the present invention. The measuring head 200 of FIG. 2 illustratively comprises a hexagonally shaped housing 202 having a sampling aperture 204 on a front face. The measuring head 200 of FIG. 2 illustratively comprises six flat mirrors $210_1$-$210_6$ illustratively located 60 degrees apart in a substantially circular pattern, six collimating optics $220_1$-$220_6$ (illustratively a respective collimating lens for each flat mirror), a focusing optic 230 (illustratively a focusing lens) and seven optical fibers $240_1$-$240_7$. FIG. 2 further depicts an incandescent light source (illustratively a Xenon flash lamp) 250. The light source 250 may be included as a component of the measuring head 200 or may be provided by a user.

In the measuring head 200 of FIG. 2 as in the measuring head 100 of FIG. 1, light from the Xenon lamp 250 is collected by the input optical fibers, illustratively optical fibers $240_1$-$240_6$. The light from the Xenon lamp 250 collected by each of the input optical fibers $240_1$-$240_6$ is directed to a respective flat mirror $210_1$-$210_6$ of the measuring head 200. The light from the respective input fibers $240_1$-$240_6$ reflects off of the respective flat mirror $210_1$-$210_6$ to a respective collimating lens $220_1$-$220_6$. The light from each of the input fibers $240_1$-$240_6$ collimated by the respective collimating lenses $220_1$-$220_6$ illuminates a sample via the sampling aperture 204 of the cylindrical housing 202 of the measuring head 200 at an angle of substantially 45 degrees, in one embodiment. Diffused light generated by the illumination of the sample via the sampling aperture 204 is collected perpendicularly and focused by the focusing lens 230 and is collected by the seventh optical fiber $240_7$ (output optical fiber), which directs the collected light outside of the measuring head. The light in the output optical fiber $240_7$ is carried outside of the measuring head 200 by the seventh optical fiber $240_7$ to be used, for example, by a measuring instrument for the spectral analysis of the collected light. The inventors determined that by implementing a plurality of combinations of light guides and flat mirrors to illuminate a sample, a sample may be illuminated with greater intensity resulting in, for example, greater accuracy in the spectral analysis of the collected light by a measuring instrument.

Figure 3:
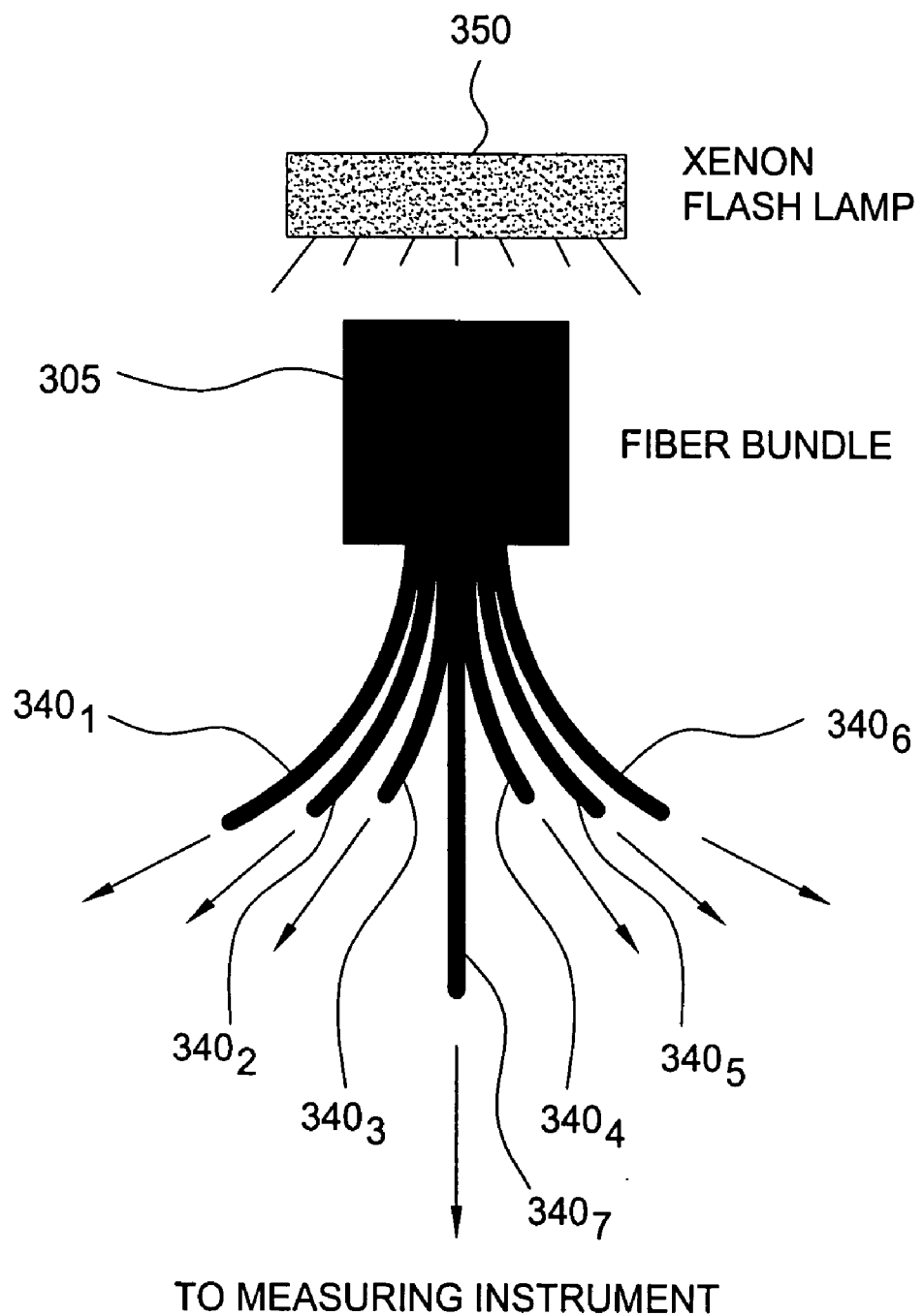
FIG. 3. depicts a high level block diagram of an embodiment of a fiber bundle suitable for use with a measuring head in accordance with the present invention.

To reduce the form factor required by a measuring head of the present invention, the input and output optical fibers may comprise a fiber bundle. For example, FIG. 3 depicts a high level block diagram of an embodiment of a fiber bundle 300 suitable for use with, for example, the measuring head 200 of FIG. 2. The fiber bundle 300 of FIG. 3 comprises a core light collector 305 and seven light guides (illustratively seven optical fibers) $340_1$-$340_7$ branching off of the core light collector 305. FIG. 3 further depicts a Xenon light flash lamp 350 for descriptive purposes. As depicted in FIG. 3, the light collector 305 is placed in a position in front of the Xenon lamp 350 to collect a maximum amount of light from the Xenon lamp 350. Six input optical fibers, illustratively optical fibers $340_1$-$340_6$, carry the light from the Xenon lamp 350 to a measuring head, such as the measuring head 200 of FIG. 2, to illuminate a sample as described above. The seventh optical fiber $340_7$ of the fiber bundle 300 is implemented to collect the diffused light from the sample and carry the collected light outside of the measuring head to be used, for example, by a measuring instrument for the spectral analysis of the collected light.

The implementation of optical light guides (e.g., optical fibers and/or fiber bundles) in a measuring head, in accordance with the present invention, provides many advantages over conventional measuring heads. For example, the optical light guides of the present invention provide flexibility in the positioning of a light source with respect to a measuring head of the present invention. More specifically, the position of a measuring head of the present invention relative to the light source is not as critical as in conventional measuring heads because of the flexibility provided by the light guide (s) implemented to carry light from a light source into the measuring head. Additionally the light guide(s) implemented to collect the diffused light from an illuminated sample and to carry the collected light outside of the measuring head provides further flexibility in the positioning of a measuring head of the present invention with respect to, for example, a measuring instrument used for the spectral analysis of the collected light. As such, the position of the measuring head when illuminating a sample may be varied instead of having to stay fixed with respect to a light source and a subsequent measuring instrument as in conventional measuring heads. To allow for any flexibility in the positioning of conventional measuring heads, a light source was often included in the housing of conventional measuring heads, which greatly increases the form factor of the conventional measuring heads as compared to the small form factor of the present invention. In addition, the implementation of optical fibers or fiber bundles allows light from an external light source to enter a measuring head substantially parallel to its axis and still be bent outward, for example at a 45 degree angle as depicted in FIG. 1, without additional light scattering or other losses. Conventional measuring heads require at least an additional reflecting surface for such an implementation which can incur additional light scattering or other losses.

Figure 4:
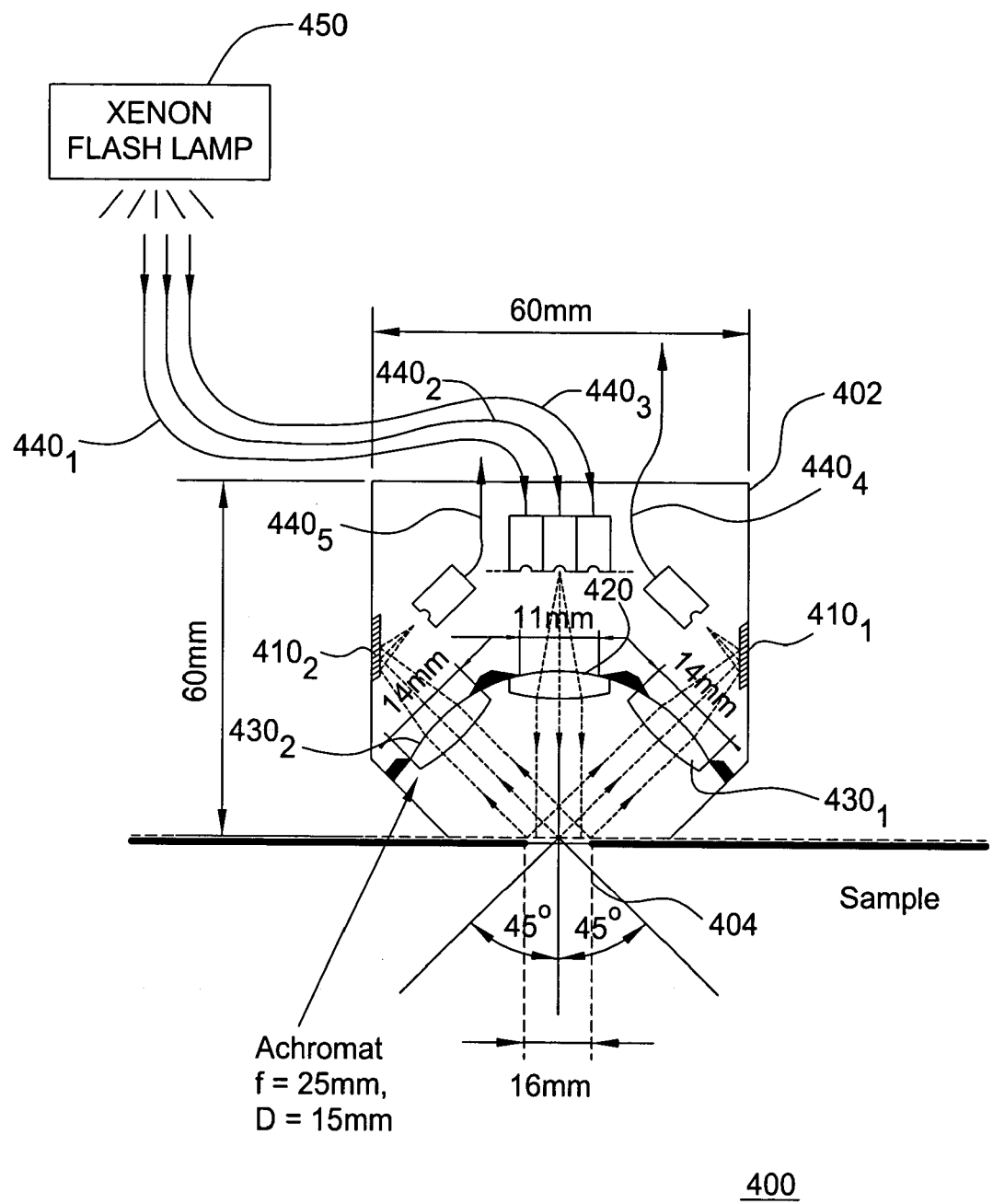
FIG. 4 depicts a high level block diagram of an alternate embodiment of a measuring head in accordance with the present invention.

FIG. 4 depicts a high level block diagram of an alternate embodiment of a measuring head in accordance with the present invention. More specifically, FIG. 4 depicts an embodiment of a 0/45 degree measuring head in accordance with the present invention. In the measuring head 400 of FIG. 4, a sample is illuminated at substantially zero degrees and the diffused light is focused and collected at substantially forty-five degrees. The measuring head 400 of FIG. 4 illustratively comprises substantially the same components as the measuring head 100 of FIG. 1, however in the measuring head 400 of FIG. 4, the input optical fibers are now implemented as output optical fibers and the output optical fibers are implemented as input optical fibers. More specifically, the measuring head 400 of FIG. 4 illustratively comprises a housing 402 having a sampling aperture 404 on a front face. The measuring head 400 further comprises two flat mirrors $410_1$-$410_2$ illustratively located 180 degrees apart on opposite side walls, a collimating optic 420 (illustratively a collimating lens), two focusing optics $430_1$-$430_2$ (illustratively a focusing lens for each flat mirror) and five light guides (illustratively five optical fibers) $440_1$-$440_5$. FIG. 1 further depicts an incandescent light source (illustratively a Xenon flash lamp) 450. The light source 450 may be included as a component to be used with the measuring head 100 or may be provided by a user.

In the measuring head 400 of FIG. 4, light from the Xenon lamp 450 is collected by three of the optical fibers (input optical fibers), illustratively optical fibers $440_1$-$440_3$. The light from the Xenon lamp 450 collected by the input optical fibers $440_1$-$440_3$ is used to illuminate a sample an angle of substantially 0°+/−0.5°. More specifically, the light from the Xenon lamp 450 collected by the input optical fibers $440_1$-$440_3$ is collected and collimated by the collimating lens 420. The collimated light then illuminates a sample via the sampling aperture 404 of the housing 402 of the measuring head 400. Diffused light generated by the illumination of the sample via the aperture 404 is incident on and reflected by each of the flat mirrors $410_1$-$410_2$ at an angle of substantially 45°+/−2°. More specifically, the perpendicularly illuminated sample diffuses light in various directions at an angle of substantially 45°+/−2°. The diffused light is incident on each of the two each of the two flat mirrors $410_1$-$410_2$ at an angle of 45°+/−2° and is reflected by each of the two flat mirrors $410_1$-$410_2$ at an angle of substantially 45°+/−2°. The collimated light reflected by the two flat mirrors $410_1$-$410_2$ is collected by a respective focusing lens $430_1$-$430_2$. Each of the focusing lenses $430_1$-$430_2$ focuses the collimated beam to a spot. At the focal position of the focusing lenses $430_1$-$430_2$, the focused, diffused light from each of the focusing lenses $430_1$-$430_2$ is collected by a respective optical fiber $440_4$ and $440_5$ (output optical fibers), which carry the collected light outside of the measuring head. The light in the output optical fibers $440_4$-$440_5$ is carried outside of the measuring head by the output fibers $440_4$-$440_5$ to be used, for example, by a measuring instrument for the spectral analysis of the collected light. In various embodiments of the present invention, the output optical fibers may take the form of a 1:N optical fiber where the plurality of output optical fibers implemented to collect the diffused, focused light from the illuminated sample comprise a plurality of optical fibers on one end and a single optical fiber on the other.

Although embodiments of the present invention are described above with reference to a 45/0 degree measuring head and a 0/45 degree measuring head, the angles for the illumination of a sample and for the collection of the diffused light from the sample depicted in the embodiments of the present invention described above are only exemplary and should not be treated as limiting the scope of the invention. It will be appreciated by those skilled in the art informed by the teachings of the present invention that the concepts of the present invention may be advantageously applied to a measuring head implementing substantially any angle for illuminating a sample and substantially any angle for collecting the diffused light from a sample. The 45/0 degree and 0/45 degree illumination and collection angles are merely standard practice in the art and are taught by the American Society for Testing and Materials (ASTM) and by the International Illumination Commission (CIE) as standards for illumination and collection, for example, in defining color measurements.

While the foregoing is directed to embodiments of the present invention, other and further embodiments of the invention may be devised without departing from the basic scope thereof, and the scope thereof is determined by the claims that follow.

The invention claimed is:

1. A measuring head, comprising:
   at least one input light guide for conveying light from an external light source to said measuring head for the illumination of a sample;
   at least one plane mirror for reflecting said conveyed light from said external light source such that an optical path of said conveyed light is folded at least once within said measuring head;
   at least one collimating optic for collimating the light reflected by said at least one plane mirror;
   light baffles for baffling portions of said conveyed light from said at least one input light guide, wherein said light baffles are positioned at the lateral edges of said at least one collimating optic; and
   at least one focusing optic for focusing diffused light from said illuminated sample.

2. The measuring head of claim 1, further comprising:
   at least one output light guide for collecting the focused light.

3. The measuring head of claim 2, wherein said at least one input light guide conveys light from said external light source to said at least one collimating optic, said at least one collimating optic collimates the conveyed light, said sample is illuminated by said collimated light from said collimating optic, said focusing optic focuses said diffused light from said illuminated sample to a spot within said measuring head, and said at least one output light guide collects said focused light at the focal position of said focusing optic and conveys said collected light outside of said measuring head.

4. The measuring head of claim 3, wherein said sample is illuminated by said collimated light at an angle of substantially forty-five degrees and the diffused light from said illuminated sample is collected at an angle of substantially zero degrees.

5. The measuring head of claim 3, wherein said sample is illuminated by said collimated light at an angle of substantially zero degrees and the diffused light from said illuminated sample is collected at an angle of substantially forty-five degrees.

6. The measuring head of claim 2, wherein said at least one input light guide and said at least one output light guide comprise optical fibers.

7. The measuring head of claim 6, wherein said at least one input optical fiber and said at least one output optical fiber comprise a fiber bundle.

8. The measuring head of claim 1, wherein said at least one collimating optic comprises a collimating lens.

9. The measuring head of claim 1, wherein said at least one focusing optic comprises a focusing lens.

10. The measuring head of claim 1, wherein said external light source comprises an incandescent light source.

11. The measuring head of claim 10, wherein said incandescent light source comprises a Xenon flash lamp.

12. The measuring head of claim 2, wherein said at least one output optical fiber conveys said collected light to a spectrometer for spectral analysis of said collected light.

13. The measuring head of claim 1, wherein said measuring head comprises six input light guides and six respective plane mirrors for conveying light from an external light source to a sample for the illumination of said sample.

14. The measuring head of claim 13, wherein said six respective plane mirrors are positioned sixty degrees apart in said measuring head.

15. The measuring head of claim 13, further comprising six respective collimating optics for collimating the reflected light from each of the plane mirrors.

16. The measuring head of claim 1, wherein said light baffles are additionally positioned at the edges of said at least one focusing optic.

17. The measuring head of claim 1, wherein said measuring head includes an aperture in a front face for the illumination of said sample.

18. The measuring head of claim 2, wherein said at least one input light guide and said at least one output light guide respectively enter and exit said measuring head parallel to a measuring axis of said measuring head.

19. A method for illuminating a sample, comprising:

providing an external light source; and illuminating said sample using said external light source via a measuring head, said measuring head comprising;

at least one input light guide for conveying light from said external light source into said measuring head;

at least one plane mirror for reflecting said conveyed light from said external light source such that an optical path of said conveyed light is folded at least once within said measuring head;

at least one collimating optic for collimating the light reflected by said at least one plane mirror;

light baffles for baffling portions of said conveyed light from said at least one input light guide, wherein said light baffles are positioned at the lateral edges of said at least one collimating optic; and at least one focusing optic for focusing diffused light from said illuminated sample.

20. The method of claim 19, further comprising:

collecting the focused, diffused light via at least one output light guide.

* * * * *